United States Patent [19]

Anderson

[11] 4,307,113
[45] Dec. 22, 1981

[54] ANTHRANILIC ACID DERIVATIVES

[75] Inventor: Paul L. Anderson, Dover, N.J.

[73] Assignee: Sandoz, Inc., East Hanover, N.J.

[21] Appl. No.: 114,044

[22] Filed: Jan. 21, 1980

Related U.S. Application Data

[63] Continuation-in-part of Ser. No. 38,419, May 14, 1979, abandoned, which is a continuation-in-part of Ser. No. 898,160, Apr. 20, 1978, abandoned.

[51] Int. Cl.³ .................. A61K 31/245; A61K 31/195
[52] U.S. Cl. ...................................... 424/310; 424/319
[58] Field of Search ........................ 424/310, 317, 319

[56] References Cited

U.S. PATENT DOCUMENTS

| | | | |
|---|---|---|---|
| 3,268,394 | 8/1966 | Weil et al. | 424/310 |
| 3,422,200 | 1/1969 | Rogers et al. | 424/310 |
| 3,657,436 | 4/1972 | Berger et al. | 424/244 |
| 3,868,416 | 2/1975 | Albright et al. | 260/518 R |
| 3,869,553 | 3/1975 | Holland | 424/317 |
| 4,143,151 | 3/1979 | Wagner et al. | 424/275 |

FOREIGN PATENT DOCUMENTS 2258367 11/1976 France ................................ 424/317

OTHER PUBLICATIONS

*Mie Medical Journal*, vol. XVII, No. 1, 1967, pp. 83-92.
Research Chemicals Catalog, p. 96 (1976), Pfaltz and Bauer.
Journal of Medicinal and Pharmaceutical Chemistry, vol. 1, No. 2, (1959), 121.

*Primary Examiner*—Frederick E. Waddell
*Attorney, Agent, or Firm*—Gerald D. Sharkin; Richard E. Vila; Joseph J. Borovian

[57] ABSTRACT

Agents for lowering glucose levels in blood having the formula:

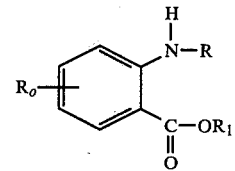

wherein
$R_o$ is bromo, chloro, fluoro, nitro or trifluoromethyl,
R is hydrogen, $C_{1-6}$ alkyl or $C_{2-18}$ alkanoyl, and
$R_1$ is hydrogen or $C_{1-12}$ alkyl, and the non-toxic, pharmaceutically acceptable salts thereof.

28 Claims, No Drawings

ANTHRANILIC ACID DERIVATIVES

This application is a continuation-in-part of U.S. application Ser. No. 38,419, filed May 14, 1979, which in turn is a continuation-in-part of U.S. application Ser. No. 898,160, filed Apr. 20, 1978, both now abandoned.

The present invention relates to certain anthranilic acid derivatives, pharmaceutically acceptable salts thereof, where such may exist, and to their use as hypoglycemic agents. The invention also relates to pharmaceutical compositions containing the above compounds as an active ingredient thereof and to the method of using such compositions for lowering blood glucose levels in, e.g., the treatment of diabetes.

European Pat. No. 3,532 discloses ω-2-benzamidophenylalkanoic acids exhibiting hypoglycemic and hepatic glucose synthesis inhibiting activity.

The compounds N-benzyl-6-chloroanthranilic and N-benzoyl-6-chloroanthranilic acid are disclosed in Chem. Pharm. Bull. 27(6) 1468–1472 (1979) as exhibiting hypoglycemic activity.

The compound N-acetyl-5-trifluoromethylanthranilic acid has been described in U.S. Pat. No. 3,869,553, which is directed to polysubstituted benzoic acids useful as hypolipemic agents.

The compounds 5-chloroanthranilic acid, N-acetyl-3-chloroanthranilic acid, N-acetyl-5-chloroanthranilic acid, N-acetyl-6-chloroanthranilic acid and N-acetyl-5-bromoanthranilic acid are disclosed in U.S. Pat. No. 3,657,436, which is directed to anthranilic acid derivatives useful as anti-viral agents.

The compounds 5-chloroanthranilic acid and 5-fluoroanthranilic acid are disclosed in Mie Med. J. 17, 83–92 (1967), which is directed to a study of the anti-cancer effects of various analogues of anthranilic acid.

In addition, the compounds 3-, 4-, 5- and 6-trifluoromethylanthranilic acid have been previously disclosed in French Pat. No. 2,258,367; the compounds 3-, 4-, 5- and 6-nitroanthranilic acid have been previously disclosed in the Handbook of Chemistry and Physics, p. C-184, 47th Edition (1966–67); the compound N-acetyl-4-nitroanthranilic acid has been disclosed in Alfred Bader Chemicals, p. 122 (1975); and the compounds 4-chloroanthranilic acid and 5-chloroanthranilic acid, methyl ester have been described in Pfaltz and Bauer, Research Chemicals Catalog, p. 96 (1976). To my knowledge, however, no pharmacological activity has been heretofore associated with any of these compounds.

One aspect of the present invention involves the use of the compounds of formula I:

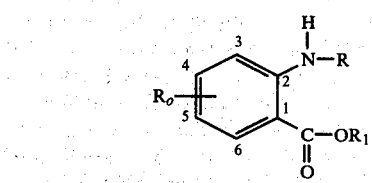

wherein
$R_o$ is bromo, chloro, fluoro, nitro or trifluoromethyl,
R is hydrogen, $C_{1-6}$ alkyl or $C_{2-18}$ alkanoyl, and
$R_1$ is hydrogen or $C_{1-12}$ alkyl,
and the non-toxic, pharmaceutically acceptable salts thereof, as hypoglycemic agents in, e.g., the treatment of diabetes.

Representative of such compounds are those wherein $R_o$ is bromo, chloro, fluoro, nitro or trifluoromethyl; R is hydrogen $C_{1-6}$ alkyl or $C_{2-4}$ alkanoyl; and $R_1$ is hydrogen or $C_{1-6}$ alkyl, and the non-toxic, pharmaceutically acceptable salts thereof.

Included among the class of compounds of formula I are the compounds of subclass Ia:

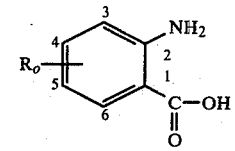

wherein $R_o$ is as defined above with respect to the compounds of formula I, and the non-toxic, pharmaceutically acceptable salts thereof. Preferred compounds of subclass Ia are compounds wherein $R_o$ is chloro, nitro or trifluoromethyl, especially those wherein $R_o$ is trifluoromethyl, and the non-toxic, pharmaceutically acceptable salts thereof. The more preferred compounds of subclass Ia are compounds wherein $R_o$ is chloro, nitro or trifluoromethyl in the 4- or 6-position, especially those wherein $R_o$ is trifluoromethyl in the 4- or 6-position, and the non-toxic, pharmaceutically acceptable salts thereof. The even more preferred compounds of subclass Ia are compounds wherein $R_o$ is chloro, nitro or trifluoromethyl in the 4-position, and the non-toxic, pharmaceutically acceptable salts thereof. The most preferred compound of subclass Ia is 4-trifluoromethylanthranilic acid.

Also included among the class of compounds of formula I are the compounds of subclass Ib:

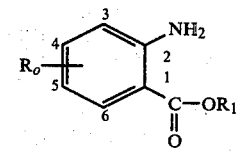

wherein $R_o$ is as defined above with respect to the compounds of formula I and $R_1$ is $C_{1-12}$ alkyl, and the non-toxic, pharmaceutically acceptable acid addition salts thereof. Preferred compounds of subclass Ib are compounds wherein $R_o$ is chloro, nitro or trifluoromethyl and $R_1$ is $C_{1-12}$ alkyl, especially those wherein $R_o$ is trifluoromethyl and $R_1$ is $C_{1-12}$ alkyl, and the non-toxic, pharmaceutically acceptable acid addition salts thereof. The more preferred compounds of subclass Ib are compounds wherein $R_o$ is chloro, nitro or trifluoromethyl in the 4- or 6-position and $R_1$ is $C_{1-8}$ alkyl, especially those wherein $R_o$ is trifluoromethyl in the 4- or 6-position and $R_1$ is $C_{1-8}$ alkyl, and the non-toxic, pharmaceutically acceptable acid addition salts thereof. The even more preferred compounds of subclass Ib are compounds wherein $R_o$ is chloro, nitro or trifluoromethyl in the 4-position and $R_1$ is $C_{1-6}$ alkyl, and the non-toxic, pharmaceutically acceptable acid addition salts thereof. The most preferred compound of subclass Ib is 4-trifluoromethylanthranilic acid hexyl ester.

Representative compounds of subclass Ib are those wherein $R_o$ is as defined above with respect to the compounds of formula I and $R_1$ is $C_{1-6}$ alkyl, and the non-toxic, pharmaceutically acceptable acid addition salts thereof. Further representative of such compounds are those wherein $R_o$ is chloro, nitro or trifluoromethyl, especially in the 4-position, more especially trifluorometyl in the 4-position, and $R_1$ is $C_{1-4}$ alkyl, especially those of each of these groups wherein $R_1$ is methyl or ethyl, and the non-toxic, pharmaceutically acceptable acid addition salts thereof.

Further representative of the class of compounds of formula I are the compounds of subclass Ic:

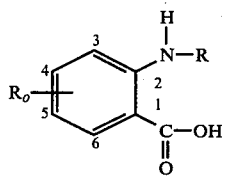

wherein $R_o$ is as defined above with respect to the compounds of formula I and R is $C_{2-18}$ alkanoyl or $C_{1-6}$ alkyl, and the non-toxic, pharmaceutically acceptable salts thereof. Preferred compounds of subclass Ic are compounds wherein R is $C_{2-18}$ alkanoyl and $R_o$ is chloro, nitro or trifluoromethyl, preferably in the 4- or 6-position, especially those wherein R is $C_{2-18}$ alkanoyl and $R_o$ is trifluoromethyl, preferably in the 4- or 6-position, and the non-toxic, pharmaceutically acceptable simple salts thereof. The more preferred compounds of subclass Ic are compounds wherein R is $C_{2-12}$ alkanoyl and $R_o$ is chloro, nitro or trifluoromethyl in the 4- or 6-position, especially those wherein R is $C_{2-12}$ alkanoyl and $R_o$ is trifluoromethyl in the 4- or 6-position, and the non-toxic, pharmaceutically acceptable simple salts thereof. The even more preferred compounds of subclass Ic are compounds wherein R is $C_{2-8}$ alkanoyl and $R_o$ is chloro, nitro or trifluoromethyl in the 4-position, especially those wherein R is $C_{2-8}$ alkanoyl and $R_o$ is trifluoromethyl in the 4-position, and the non-toxic, pharmaceutically acceptable simple salts thereof. The most preferred compounds of subclass Ic are N-acetyl-4-trifluoromethylanthranilic acid and N-caproyl-4-trifluoromethylanthranilic acid.

Representative compounds of subclass Ic are those wherein $R_o$ is as defined above with respect to the compounds of formula I and R is $C_{2-4}$ alkanoyl or $C_{1-6}$ alkyl, and the non-toxic, pharmaceutically acceptable salts thereof. Further representative of such compounds are those wherein $R_o$ is chloro, nitro or trifluoromethyl, especially in the 4-position, and R is $C_{2-4}$ alkanoyl, especially acetyl, and the non-toxic, pharmaceutically acceptable simple salts thereof.

Also representative of the class of compounds of formula I are the compounds of subclass Id:

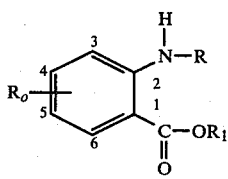

wherein $R_o$ is as defined above with respect to the compounds of formula I, R is $C_{2-18}$ alkanoyl or $C_{1-6}$ alkyl and $R_1$ is $C_{1-12}$ alkyl, and the non-toxic, pharmaceutically acceptable acid addition salts thereof. Preferred compounds of subclass Id are compounds wherein $R_o$ is chloro, nitro or trifluoromethyl, R is $C_{2-18}$ alkanoyl and $R_1$ is $C_{1-12}$ alkyl, especially those wherein $R_o$ is trifluoromethyl, R is $C_{2-18}$ alkanoyl and $R_1$ is $C_{1-12}$ alkyl. The more preferred compounds of subclass Id are compounds wherein $R_o$ is chloro, nitro or trifluoromethyl in the 4- or 6-position, R is $C_{2-12}$ alkanoyl and $R_1$ is $C_{1-8}$ alkyl, especially those wherein $R_o$ is trifluoromethyl in the 4- or 6-position, R is $C_{2-12}$ alkanoyl and $R_1$ is $C_{1-8}$ alkyl. The even more preferred compounds of subclass Id are compounds wherein $R_o$ is chloro, nitro or trifluoromethyl in the 4-position, R is $C_{2-8}$ alkanoyl and $R_1$ is $C_{1-6}$ alkyl, especially those wherein $R_o$ is trifluoromethyl in the 4-position, R is $C_{2-8}$ alkanoyl and $R_1$ is $C_{1-6}$ alkyl.

Representative compounds of subclass Id are those wherein $R_o$ is as defined above with respect to the compounds of formula I, R is $C_{2-4}$ alkanoyl or $C_{1-6}$ alkyl, especially $C_{2-4}$ alkanoyl, and $R_1$ is $C_{1-6}$ alkyl, and the non-toxic, pharmaceutically acceptable acid addition salts thereof.

Another aspect of the present invention involves the novel compositions comprising a compound of formula I:

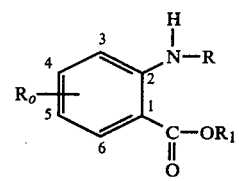

wherein $R_o$ is bromo, chloro, fluoro, nitro or trifluoromethyl,
R is hydrogen, $C_{1-6}$ alkyl or $C_{2-18}$ alkanoyl, and
$R_1$ is hydrogen or $C_{1-12}$ alkyl,
or a non-toxic, pharmaceutically acceptable salt thereof, with the provisos that:

(1) when each of R and $R_1$ is hydrogen, $R_o$ is other than 5-chloro; and (2) when R is acetyl and $R_1$ is hydrogen, $R_o$ is other than 5- or 6-chloro, 5-bromo or 5-trifluoromethyl,
and a pharmaceutically acceptable carrier.

Preferred compositions are those comprising a compound of formula I wherein $R_o$ is chloro, nitro or trifluoromethyl in the 4- or 6-position, R is hydrogen or $C_{2-18}$ alkanoyl and $R_1$ is hydrogen or $C_{1-12}$ alkyl, or a non-toxic, pharmaceutically acceptable salt thereof, and a pharmaceutically acceptable carrier. The more preferred compositions are those comprising a compound of formula I wherein $R_o$ is chloro, nitro or trifluoromethyl in the 4-position, R is hydrogen or $C_{2-12}$ alkanoyl and $R_1$ is hydrogen or $C_{1-8}$ alkyl, or a non-toxic, pharmaceutically acceptable salt thereof, and a pharmaceutically acceptable carrier. The even more preferred compositions are those comprising a compound of formula I wherein $R_o$ is trifluoromethyl in the 4-position, R is hydrogen or $C_{2-8}$ alkanoyl and $R_1$ is hydrogen or $C_{1-6}$ alkyl, or a non-toxic, pharmaceutically acceptable salt thereof, and a pharmaceutically acceptable carrier. The most preferred compositions are those comprising 4-chloro-, 4-nitro or 4-trifluoromethylanthranilic acid, 4-trifluoromethylanthranilic acid hexyl ester, N-acetyl-4-trifluoromethylanthranilic acid or N-caproyl-4-trifluoromethylanthranilic acid, and a pharmaceutically acceptable carrier.

Other representative compositions are those comprising a compound of formula I wherein $R_o$ is bromo, chloro, fluoro, nitro or trifluoromethyl; R is hydrogen, $C_{1-6}$ alkyl or $C_{2-4}$ alkanoyl; and $R_1$ is hydrogen or $C_{1-6}$ alkyl, or a non-toxic, pharmaceutically acceptable salt thereof, with the provisos that:

(1) when each of R and $R_1$ is hydrogen, $R_o$ is other than 5-chloro; and (2) when R is acetyl and $R_1$ is hydrogen, $R_o$ is other than 5- or 6-chloro, 5-bromo or 5-trifluoromethyl, and a pharmaceutically acceptable carrier. Further representative compositions are those comprising a compound of formula I wherein $R_o$ is chloro, nitro or trifluoromethyl in the 4-position, or a non-toxic, pharmaceutically acceptable salt thereof, and a pharmaceutically acceptable carrier.

Still another aspect of the present invention involves the novel compounds of formula I':

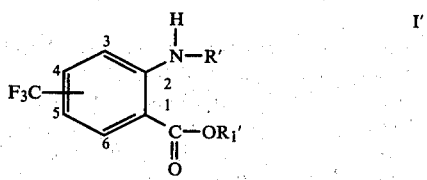

wherein R' is hydrogen, $C_{1-6}$ alkyl or $C_{2-18}$ alkanoyl, and $R_1'$ is hydrogen or $C_{1-12}$ alkyl, and the non-toxic, pharmaceutically acceptable salts thereof, with the provisos that:

(1) R' and $R_1'$ cannot both be hydrogen; and (2) when R' is acetyl and $R_1'$ is hydrogen, the —$CF_3$ group is in other than the 5-position.

Preferred compounds of formula I' are the compounds of formula I'':

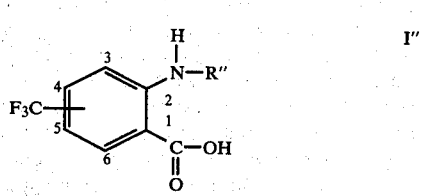

wherein R'' is $C_{2-18}$ alkanoyl and the —$CF_3$ group is in the 4- or 6-position, and the non-toxic, pharmaceutically acceptable simple salts thereof.

The more preferred compounds of formula I'' are those wherein R'' is $C_{2-12}$ alkanoyl and the —$CF_3$ group is in the 4- or 6-position, especially those wherein R'' is $C_{2-12}$ alkanoyl and the —$CF_3$ group is in the 4-position, and the non-toxic, pharmaceutically acceptable simple salts thereof.

The even more preferred compounds of formula I'' are those wherein R'' is $C_{2-8}$ alkanoyl and the —$CF_3$ group is in the 4- or 6-position, especially those wherein R'' is $C_{2-8}$ alkanoyl and the —$CF_3$ group is in the 4-position, and the non-toxic, pharmaceutically acceptable simple salts thereof.

Other preferred compounds of formula I' are the compounds of formula I''':

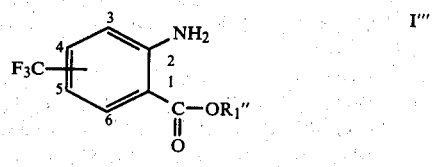

wherein $R_1''$ is $C_{1-12}$ alkyl and the —$CF_3$ group is in the 4- or 6-position, and the non-toxic, pharmaceutically acceptable acid addition salts thereof.

The more preferred compounds of formula I''' are those wherein $R_1''$ is $C_{1-8}$ alkyl and the —$CF_3$ group is in the 4- or 6-position, especially those wherein $R_1''$ is $C_{1-8}$ alkyl and the —$CF_3$ group is in the 4-position, and the non-toxic, pharmaceutically acceptable acid addition salts thereof.

The even more preferred compounds of formula I''' are those wherein $R_1''$ is $C_{1-6}$ alkyl and the —$CF_3$ group is in the 4- or 6-position, especially those wherein $R_1''$ is $C_{1-6}$ alkyl and the —$CF_3$ group is in the 4-position, and the non-toxic, pharmaceutically acceptable acid addition salts thereof.

Other representative compounds of formula I' are those wherein R' is hydrogen, $C_{1-6}$ alkyl or $C_{2-4}$ alkanoyl and $R_1'$ is $C_{1-6}$ alkyl, and the non-toxic, pharmaceutically acceptable acid addition salts thereof. Further representative compounds of formula I' are those wherein R' is hydrogen or $C_{1-4}$ alkyl and $R_1'$ is $C_{1-4}$ alkyl, and the non-toxic, pharmaceutically acceptable acid addition salts thereof. Still further representative compounds of formula I' are those wherein R' is hydrogen, methyl or ethyl and $R_1'$ is methyl or ethyl, and the non-toxic, pharmaceutically acceptable acid addition salts thereof, especially those compounds wherein the —$CF_3$ group is in the 4-position. Yet still further representative compounds of formula I' are those wherein R' is hydrogen and $R_1'$ is ethyl, and the non-toxic, pharmaceutically acceptable acid addition salts thereof, especially those compounds wherein the —$CF_3$ group is in the 4-position.

The compounds of subclass Ia may be prepared by hydrolysis (process (a)) of an amine-amide compound of formula II:

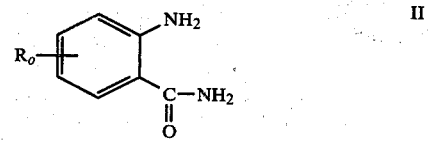

wherein $R_o$ is as defined above with respect to the compounds of formula I. Thus, the preparation of compounds of formula Ia involves subjecting a compound of formula II to either acidic or alkaline hydrolysis, i.e., the anthranilic acid amide compound is treated with either an aqueous inorganic acid or, in the case of alkaline hydrolysis, an alkali or alkaline earth metal carbonate or hydroxide, ammonium hydroxide or is reacted with a mono-, di- or tri- ($C_2$–$C_4$) alkanol ammonium compound or a mono-, di-, tri- or tetra- ($C_1$–$C_4$) alkylammonium compound. The inorganic acid employed can be any mineral acid, such as sulfuric acid, hydrochloric acid and the like, preferably, in dilute form. As regards alkaline hydrolysis, preferred are the alkali metal carbonates and hydroxides, more preferably the latter and most preferably, sodium or potassium hydroxide. The hydrolysis is conveniently carried out at a temperature of from 0° to 100° C., preferably 80° to 100° C., for a period of between 1 and 24 hours, preferably, 1 to 5 hours. As is fairly evident, when a compound of formula II undergoes alkaline hydrolysis, the simple salts of the compounds of formula Ia are produced, which salts, if pharmaceutically acceptable, are embraced by the scope of the present invention. Thus, to produce a compound of formula Ia, in free acid form, the salt is acidified under mild acidic conditions, suitably using hydrochloric or sulfuric acid, preferably, hydrochloric acid.

It will be noted that compounds Ia bear a free amino group and can, therefore, form non-toxic, pharmaceutically acceptable acid addition salts; it being understood that such salts are comprehended as being included within the scope of the present invention.

The compounds of subclass Ib may be prepared by esterifying (process (b)) a compound of formula Ia by reaction with an alcohol, i.e., a compound of formula III:

$$HO-R_1 \qquad\qquad III$$

wherein $R_1$ is $C_{1-12}$ alkyl, under conditions conventionally employed in esterifying a carboxylic acid function. Process (b) may conveniently be carried out in an inert organic solvent, for example, an aromatic hydrocarbon such as toluene, benzene or xylene, in the presence of an acidic catalyst such as an aromatic sulfonic acid, e.g., p-toluenesulfonic acid, at elevated temperatures, e.g., from 100° to 200° C., under conditions in which water formed in the reaction is removed from the system, e.g., by carrying out process (b) in an extractor apparatus charged with a drying agent. It is particularly convenient to carry out the esterification at the reflux temperature of the reaction mixture, when such falls within a suitable range. Reaction times will, of course, vary with the nature of the reactants and the reaction conditions employed, but it is preferred to carry out the reaction at more moderate temperatures, e.g., at from about 120° to 150° C. over an extended period of time, e.g., for from about 1 to 20 days.

As with respect to the compounds of subclass Ia, the compounds of subclass Ib also bear a free amino group and can, therefore, form non-toxic, pharmaceutically acceptable acid addition salts, which salts are intended to be embraced by the present invention.

The compounds of subclass Ic wherein $R_o$ is as defined above with respect to the compounds of formula I and R is $C_{2-18}$ alkanoyl may be prepared by alkanoylation (process (c)) of a compound of formula Ia with an alkanoylating agent, i.e., a compound of formula IV:

$$R-X \qquad\qquad IV$$

wherein R is $C_{2-18}$ alkanoyl, and X is chloro, bromo or wherein R is $C_{2-18}$ alkanoyl.

The alkanoylation of compounds Ia may be carried out by conventional techniques. The alkanoylation, thus, may be effected by processes known per se for the alkanoylation of amines. Suitable alkanoylating agents (IV) include organic acids, acyl halides and acid anhydrides and mixtures thereof. For example, where the desired alkanoyl moiety is acetyl, a preferred alkanoylating agent is acetic anhydride. In carrying out the alkanoylation, inert solvent may be employed or excess alkanoylating agent may serve as solvent. In addition, an acid binding agent, e.g., pyridine, may be employed. The alkanoylation is conveniently carried out at temperatures of between −10° and 100° C., preferably between 50° and 100° C. If desired, more stringent conditions may be used, characterized by the presence of a strongly acidic catalyst, e.g., p-toluenesulfonic acid. The amount of alkanoylating agent employed is at least the chemical equivalent required for the alkanoylation, and preferably, a substantial excess.

It should be noted that the above-described compounds of subclass Ic bear a carboxylic acid group, and can, therefore, form pharmaceutically acceptable simple salts under mild, basic conditions, suitably employing an alkali metal hydroxide, preferably, sodium hydroxide; it being understood that such salts are intended to be embraced by the present invention.

The compounds of subclass Ic wherein $R_o$ is as defined above with respect to the compounds of formula I and R is $C_{1-6}$ alkyl may be prepared by reductive alkylation (process (d)) of a compound of formula Ia with an alkyl aldehyde of formula V:

$$R'-CHO \qquad\qquad V$$

wherein R' is hydrogen or $C_{1-5}$ alkyl, in the presence of a noble metal catalyst adsorbed on carbon. Thus, a compound of formula Ia is reacted with a compound of formula V in the presence of hydrogen gas under pressure and in the presence of a catalyst such as palladium on carbon or platinum oxide on carbon. The reaction is carried out in the presence of an inert, organic solvent such as the lower alkanols, e.g., methanol, ethanol, and the like. The temperature of the reaction is not critical, but it is preferred that the reaction be run at temperatures from about 20° C. to 80° C., more preferably, from about 50° C. to 70° C. Reaction times will, of course, vary but it is preferred that the reaction be conducted between a period of 1 to 24 hours, more preferably, between 16 and 20 hours.

As with respect to the previously described compounds of subclass Ic, the above-described compounds of subclass Ic bear a carboxylic acid group and can also form pharmaceutically acceptable simple salts under mild, basic conditions, as described above. In addition, the above-described compounds of subclass Ic bear a secondary nitrogen atom, and can, therefore, form non-toxic, pharmaceutically acceptable acid addition salts instead; it being understood that both types of such salts are included within the scope of the present invention.

The compounds of subclass Id wherein $R_o$ is as defined above with respect to the compounds of formula I, R is $C_{2-18}$ alkanoyl and $R_1$ is $C_{1-12}$ alkyl may be prepared by a two-step reaction wherein a compound of formula Ia is esterified (process (b)) by reaction with a compound of formula III, as defined above, to produce a compound of formula Ib, wherein $R_o$ and $R_1$ are as defined above. The second step involves the alkanoylation (process (c)) of a compound of formula Ib by reaction with a compound of formula IV, as defined above.

Conversely, the compounds of subclass Id wherein $R_o$ is as defined above with respect to the compounds of formula I, R is $C_{2-18}$ alkanoyl and $R_1$ is $C_{1-12}$ alkyl may be prepared by a two-step reaction wherein a compound of formula Ia is alkanoylated (process (c)) by reaction with a compound of formula IV, as defined above, to produce a compound of formula Ic, wherein $R_o$ and R are as defined above. The second step involves the esterification (process (b)) of a compound of formula Ic by reaction with a compound of formula III, as defined above.

The compounds of subclass Id wherein $R_o$ is as defined above with respect to the compounds of formula I, R is $C_{1-6}$ alkyl and $R_1$ is $C_{1-12}$ alkyl may be prepared by a two-step reaction wherein a compound of formula Ia is esterified (process (b)) by reaction with a compound of formula III, as defined above, to produce a compound of formula Ib, wherein $R_o$ and $R_1$ are as defined above. The second step involves the alkylation (process (d)) of a compound of formula Ib by reaction with a compound of formula V, as defined above.

Conversely, the compounds of subclass Id wherein $R_o$ is as defined above with respect to the compounds of formula I, R is $C_{1-6}$ alkyl and $R_1$ is $C_{1-12}$ alkyl may be prepared by a two-step reaction wherein a compound of formula Ia is alkylated (process (d)) by reaction with a compound of formula V, as defined above, to produce a compound of formula Ic, wherein $R_o$ and R are as defined above. The second step involves the esterification (process (b)) of a compound of formula Ic by reaction with a compound of formula III, as defined above.

It should be noted that the compounds of subclass Id wherein R is $C_{1-6}$ alkyl bear a secondary nitrogen atom and can, therefore, form non-toxic, pharmaceutically acceptable acid addition salts, which salts are embraced by the scope of the present invention.

The products of the above-described reactions may be recovered and refined in conventional manner, e.g., by crystallization, distillation or chromatographic techniques, such as eluting from a chromatographic column or separating on a silica layer.

Many of the compounds of formulae II, III, IV and V are either known and obtained by methods described in the literature, or where not known, may be obtained by methods analogous to those described in the literature.

As previously indicated, pharmaceutically acceptable acid addition salts (i.e., those salts which do not significantly increase the toxicity of the basic compound) of the compounds of formulae Ia, Ib, Ic and Id where such may exist are included within the scope of this invention. Included are salts with inorganic acids, e.g., the hydrochloride, hydrobromide, hydroiodide, phosphate (including hydrogen phosphates), metaphosphate, sulfates (including hydrogen sulfate) and perchlorate salts.

As also previously indicated, pharmaceutically acceptable simple salts of the compounds of formulae Ia and Ic are included within the scope of this invention. Included are salts wherein the cation is selected from the group consisting of alkali metal, alkaline earth metal, ammonium, mono-, di- and trialkanol ammonium wherein the alkanol group contains 2 to 4 carbon atoms and mono-, di-, tri- and tetraalkylammonium wherein the alkyl group contains 1 to 4 carbon atoms. Preferred cations are those selected from the alkali metals and the alkaline earth metals. The more preferred cations are those selected from the alkali metals, most preferably, sodium and potassium.

The compounds of formula I and their non-toxic, pharmaceutically acceptable salts are useful in lowering glucose levels in plasma in, e.g., the treatment of diabetes, as indicated in groups of six mice fasted overnight and then given orally 25 to 400 milligrams per kilogram of animal body weight of test compound (Test A). Two hours after the compound is administered, the mice are anesthetized with ether and whole blood is collected via cardiac puncture. Pooled blood samples are suspended in 1.5% carboxymethyl cellulose (CMC) solution in water for assay by the Technicon Autoanalyzer potassium ferric-cyanide method #N-2b for glucose which is compared with the glucose levels for control animals treated only with 1.5% CMC solution.

The compounds of formula I and their non-toxic, pharmaceutically acceptable salts are useful in lowering glucose levels in plasma in, e.g., the treatment of diabetes, as also indicated in male 8–10 week old genetically obese diabetic mice ($C_{57}$BL/KS-db/db) exhibiting very high insulin levels with very low insulin sensitivity (Test B). The mice are divided into three groups, viz., the "control" group, the "test compound" group and the "chlorpropamide" (a known anti-diabetic standard) group. The selection of animals into each group is determined according to the degree of urine Clinistix reaction, so that each group contains a proportionate number of animals with the same degree of glucosuria. The three groups are subjected to the following experimental regimen:

(1) "control" group—mice are fed Purina powdered food for 7 days and, on the 8th day, after 16 hours of fasting, are dosed orally with 0.5% carboxymethyl cellulose vehicle;

(2) "test compound" group—mice are fed Purina powdered food containing 0.2% of the test compound for 7 days and, on the 8th day, after 16 hours of fasting, are dosed orally with 200 mg/kg. body weight of the test compound; and (3) "chlorpropamide" group—mice are fed Purina powdered food containing 0.2% of chlorpropamide for 7 days and, on the 8th day, after 16 hours of fasting, are dosed orally with 200 mg./kg. body weight of chlorpropamide.

The above-described experimental regimen was also conducted on the normal lean litter mates whose hepatic insulin receptor numbers are higher than the genetically diabetic insulin-resistant mice. Two to six hours after dosing, the animals are anesthetized with sodium hexabarbital (85 mg./kg. body weight i.p.) and blood samples are taken from the carotid artery of obese animals and by cardiac puncture from the lean animals. The blood is placed in autoanalyzer cups containing 0.025 cc. of a heparin preparation containing 1,000 units/ml. and the samples are capped, shaken and kept in ice buckets until analyzed for glucose. Plasma glucose of the obese animals and blood glucose of the lean litter mates is determined by the autoanalyzer potassium ferric-cyanide method #N-2b. Insulin levels are measured by radioimmunoassay employing the Amersham-Searle Kit.

The compounds are particularly useful in the treatment of mature onset diabetes.

The compounds of formula I and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions are oral use may contain one or more conventional adjuvants, such as sweetening agents, flavoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose and talc, granulating and disintegrating agents, e.g. starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The effective amount of active ingredient employed for lowering blood glucose levels in, e.g., the treatment of diabetes, may vary depending on the particular compound employed, the mode of administration and the severity of the condition being treated. However, in general, satisfactory results in, e.g., the treatment of diabetes, are obtained when a compound of formula I, or a pharmaceutically acceptable salt thereof, is administered at a daily dosage of from about 3.5 milligrams to about 400 milligrams per kilogram of animal body weight, p.o., preferably given in divided doses two to four times a day, or in sustained release form. For most large mammals, the total daily dosage is from about 200 milligrams to about 4000 milligrams. Unit dosage forms suitable for internal use comprise from about 50 milligrams to about 4000 milligrams, more usually 50 to 2000 milligrams, of the active compound in intimate admixture with a solid or liquid, pharmaceutically acceptable carrier.

Tablets and capsules containing the ingredients indicated below may be prepared by conventional techniques and are useful in treating diabetes, particularly mature onset diabetes, at a dose of one tablet or capsule, 2 to 4 times a day.

| Ingredients | Weight (mg.) tablet | capsule |
|---|---|---|
| 4-trifluoromethylanthranilic acid | 100 | 100 |
| tragancath | 10 | — |
| lactose | 247.5 | 300 |
| corn starch | 25 | — |
| talcum | 15 | — |
| magnesium stearate | 2.5 | — |
| Total | 400.0 | 400 |

The following pharmaceutical compositions are formulated with the indicated amount of active ingredient using conventional techniques. The injectable suspension and the oral suspension represent formulations useful as unit doses and may be administered in the treatment of diabetes, particularly mature onset diabetes. The injectable suspension is suitable for administration once or twice a day whereas the oral liquid suspension is suitably administered 2 to 4 times per day.

| Ingredients | Weight (mg.) sterile injectable suspension | oral liquid suspension |
|---|---|---|
| 4-trifluoromethylanthranilic acid | 200 | 100 |
| sodium carboxymethylcellulose U.S.P. | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, U.S.P. | — | 4.5 |
| propyl paraben, U.S.P. | — | 1.0 |
| polysorbate 80 (e.q., Tween 80), U.S.P. | 80), — | 5 |
| sorbitol solution, 70%, U.S.P. | — | 2,500 |
| buffer agent to adjust pH for desired stability | q.s. for injection, q.s. to 1 ml. | q.s. q.s. to 5 ml. |
| water | | |

The preferred pharmaceutical compositions from the standpoint of preparation and ease of administration are solid compositions, particularly liquid or hard filled capsules and tablets containing from about 100 to 200 milligrams of the active ingredient.

The following examples are merely illustrative of representative compounds encompassed by this invention and their synthesis.

EXAMPLE 1

2-amino-α,α,α-trifluoro-p-toluic acid
(4-trifluoromethylanthranilic acid)

Step A:

Preparation of 2-amino-α,α,α-trifluoro-p-toluamide (4-trifluoromethylanthranilic acid amide)

49 g. of 2-nitro-4-trifluoromethylbenzonitrile is dissolved in 200 ml. of anhydrous methanol and the resultant solution is hydrogenated in the presence of 1.5 g. of hydrogenation catalyst (10% Pd on active charcoal). After the theoretical uptake of hydrogen is achieved, the reaction mixture is filtered to remove the palladium and the solvent is removed on a rotary evaporator. The resultant residue is filtered and dried in vacuo to yield 2-amino-α,α,α-trifluoro-p-toluamide (4-trifluoromethylanthranilic acid amide), m.p. 147°–149° C.

A larger quantity of the amide compound is obtained by combining the ethyl ether washes and evaporating the combined washes in vacuo to dryness to yield 2-amino-α,α,α-trifluoro-p-toluamide, m.p. 147°–149° C.

Step B:

Preparation of 2-amino-α,α,α-trifluoro-p-toluic acid (4-trifluoromethylanthranilic acid)

Into 160 ml. of water containing 9.6 g. of sodium hydroxide is suspended 16 g. of 2-amino-α,α,α-trifluoro-p-toluamide. The solution is refluxed 5 hours, then cooled, poured onto ice and acidified to a pH of 6 with concentrated hydrochloric acid. The resultant precipitate is filtered, washed with water and dried in vacuo to yield 2-amino-α,α,α-trifluoro-p-toluic acid (4-trifluoromethylanthranilic acid), m.p. 175°–177° C.

Test A: $ED_{25}$-56.7 mg./kg.

Test B: −30% (200 mg./kg.)

EXAMPLE 2

Following essentially the procedure of Example 1, and using in place of 4-trifluoromethylanthranilic acid amide in Step B, an equivalent amount of:
(a) 4-nitroanthranilic acid amide,
(b) 4-chloroanthranilic acid amide,
(c) 3-trifluoromethylanthranilic acid amide,
(d) 5-trifluoromethylanthranilic acid amide,
(e) 6-trifluoromethylanthranilic acid amide,
(f) 5-nitroanthranilic acid amide,
(g) 5-chloroanthranilic acid amide,
(h) 6-nitroanthranilic acid amide, or
(i) 6-chloroanthranilic acid amide,
there is obtained
(a) 4-nitroanthranilic acid, m.p. 274°–275° C., Test A: $ED_{25}$-123.8 mg./kg.
(b) 4-chloroanthranilic acid, m.p. 231°–233° C., Test A: $ED_{25}$-83.3 mg./kg.
(c) 3-trifluoromethylanthranilic acid, m.p. 154°–156° C.,
(d) 5-trifluoromethylanthranilic acid, m.p. 177°–182° C.,
(e) 6-trifluoromethylanthranilic acid, m.p. 126°–130° C., Test A: −25% (200 mg./kg.)
(f) 5-nitroanthranilic acid,
(g) 5-chloroanthranilic acid,
(h) 6-nitroanthranilic acid, and
(i) 6-chloroanthranilic acid, respectively.

EXAMPLE 3

2-amino-α,α,α-trifluoro-p-toluic acid ethyl ester (4-trifluoromethylanthranilic acid ethyl ester)

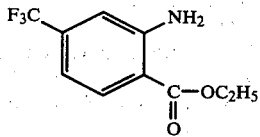

To a solution containing 5.62 g. of anhydrous p-toluenesulfonic acid pre-dissolved in 100 ml. of anhydrous ethanol and 500 ml. of benzene is added 6.1 g. of 2-amino-α,α,α-trifluoro-p-toluic acid. The solution is refluxed under an extractor containing a thimble of anhydrous magnesium sulfate for 11 days with periodic replacement of the drying agent. The resultant solution is then cooled, neutralized with 2 N sodium hydroxide and the organic layer is separated, washed with 2 N sodium hydroxide, and then with brine. After drying the organic solution over anhydrous magnesium sulfate, the solvents are removed on a rotary evaporator and the resulting crystals are dried to yield 2-amino-α,α,α-trifluoro-p-toluic acid ethyl ester (4-trifluoromethylanthranilic acid ethyl ester), m.p. 38°–39° C.

Test A: −27% (200 mg./kg.)

EXAMPLE 4

Following essentially the procedure of Example 3, and using in place of 2-amino-α,α,α-trifluoro-p-toluic acid (4-trifluoromethylanthranilic acid), an equivalent amount of:
(a) 4-nitroanthranilic acid, or
(b) 4-chloroanthranilic acid,
there is obtained
(a) 4-nitroanthranilic acid ethyl ester, and
(b) 4-chloroanthranilic acid ethyl ester, respectively.

EXAMPLE 5

2-acetamido-α,α,α-trifluoro-p-toluic acid (N-acetyl-4-trifluoromethylanthranilic acid)

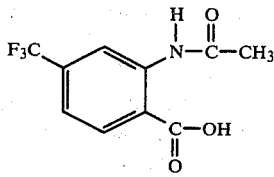

3 g. of 2-amino-α,α,α-trifluoro-p-toluic acid is dissolved in 20 ml. of acetic anhydride and the resultant solution is heated to 80° C. After 30 minutes at a temperature of 80° C., the excess acetic anhydride is removed from the reaction mixture on a rotary evaporator and water is added to the residue. The resultant precipitate is filtered, washed with water and dried to yield 2-acetamido-α,α,α-trifluoro-p-toluic acid (N-acetyl-4-trifluoromethylanthranilic acid), m.p. 195°–197° C.

Test A: −48% (200 mg./kg.)

EXAMPLE 6

Following essentially the procedure of Example 5, and using in place of 2-amino-α,α,α-trifluoro-p-toluic acid (4-trifluoromethylanthranilic acid), an equivalent amount of:
(a) 4-nitroanthranilic acid, or
(b) 4-chloroanthranilic acid,
there is obtained
(a) N-acetyl-4-nitroanthranilic acid, and
(b) N-acetyl-4-chloroanthranilic acid, respectively.

EXAMPLE 7

2-ethylamino-α,α,α-trifluoro-p-toluic acid ethyl ester (N-ethyl-4-trifluoromethylanthranilic acid ethyl ester)

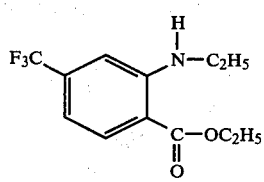

To 0.466 g. of 2-amino-α,α,α-trifluoro-p-toluic acid ethyl ester (prepared according to the procedure described in Example 2) predissolved in 20 ml. of anhydrous ethanol is added 5 ml. of 31% aqueous acetaldehyde and 46 mg. of 10% palladium on carbon. The resultant mixture is then hydrogenated at 60° for 18 hours. The reaction mixture is then cooled, filtered, the solvent removed, and the resultant oil is chromatographed on preparative thin layer plates to yield 2-ethylamino-α,α,α-trifluoro-p-toluic acid ethyl ester (N-ethyl-4-trifluoromethylanthranilic acid ethyl ester).

EXAMPLE 8

Following essentially the procedure of Example 3, and using in place of anhydrous ethanol, an equivalent amount of anhydrous hexanol, there is obtained 4-trifluoromethylanthranilic acid hexyl ester, an oil.

Test A: −48% (200 mg./kg.)

EXAMPLE 9

Following essentially the procedure of Example 5, and using in place of acetic anhydride, an equivalent amount of caproic anhydride, there is obtained N-caproyl-4-trifluoromethylanthranilic acid, m.p. 162°–164° C.

Test A: −43% (200 mg./kg.)

What is claimed is:

1. A method of treating diabetes by lowering the glucose levels in blood plasma comprising administering to a diabetic host a therapeutically effective amount of a compound of formula I:

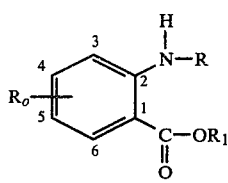

wherein
$R_o$ is bromo, chloro, fluoro, nitro or trifluoromethyl,
R is hydrogen, $C_{1-6}$ alkyl or $C_{2-18}$ alkanoyl, and
$R_1$ is hydrogen or $C_{1-12}$ alkyl,
or a pharmaceutically acceptable simple or acid addition salt thereof, said therapeutically effective amount being an amount effective for the treatment of diabetes.

2. A method of treating diabetes according to claim 1 comprising administering to a diabetic host a therapeutically effective amount of a compound of formula I wherein $R_o$ is as defined in claim 1; R is hydrogen, $C_{1-6}$ alkyl or $C_{2-4}$ alkanoyl; and $R_1$ is hydrogen or $C_{1-6}$ alkyl, or a pharmaceutically acceptable simple or acid addition salt thereof.

3. A method of treating diabetes according to claim 1 comprising administering to a diabetic host a therapeutically effective amount of a compound of formula Ia:

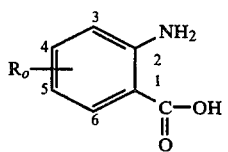

wherein $R_o$ is as defined in claim 1, or a pharmaceutically acceptable salt thereof.

4. A method of treating diabetes according to claim 3 comprising administering to a diabetic host a therapeutically effective amount of a compound wherein $R_o$ is chloro, nitro or trifluoromethyl in the 4- or 6-position, or a pharmaceutically acceptable salt thereof.

5. A method of treating diabetes according to claim 4 comprising administering to a diabetic host a therapeutically effective amount of a compound wherein $R_o$ is chloro, nitro or trifluoromethyl in the 4-position, or a pharmaceutically acceptable salt thereof.

6. A method of treating diabetes according to claim 5 comprising administering to a diabetic host a therapeutically effective amount of the compound of the formula,

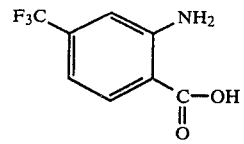

or a pharmaceutically acceptable salt thereof.

7. A method of treating diabetes according to claim 1 comprising administering to a diabetic host a therapeutically effective amount of a compound of formula Ib:

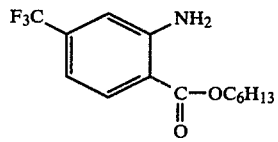

wherein $R_o$ is as defined in claim 1 and $R_1$ is $C_{1-12}$ alkyl, or a pharmaceutically acceptable acid addition salt thereof.

8. A method of treating diabetes according to claim 7 comprising administering to a diabetic host a therapeutically effective amount of a compound wherein $R_o$ is chloro, nitro or trifluoromethyl in the 4- or 6-position and $R_1$ is $C_{1-8}$ alkyl, or a pharmaceutically acceptable acid addition salt thereof.

9. A method of treating diabetes according to claim 8 comprising administering to a diabetic host a therapeutically effective amount of a compound wherein $R_o$ is chloro, nitro or trifluoromethyl in the 4-position and $R_1$ is $C_{1-6}$ alkyl, or a pharmaceutically acceptable acid addition salt thereof.

10. A method of treating diabetes according to claim 9 comprising administering to a diabetic host a therapeutically effective amount of the compound of the formula,

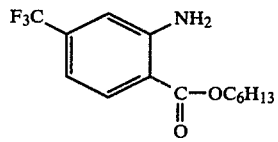

or a pharmaceutically acceptable acid addition salt thereof.

11. A method of treating diabetes according to claim 7 comprising administering to a diabetic host a therapeutically effective amount of a compound wherein $R_o$ is as defined in claim 7 and $R_1$ is $C_{1-6}$ alkyl, or a pharmaceutically acceptable acid addition salt thereof.

12. A method of treating diabetes according to claim 11 comprising administering to a diabetic host a therapeutically effective amount of a compound wherein $R_o$ is chloro, nitro or trifluoromethyl in the 4-position and $R_1$ is $C_{1-4}$ alkyl, or a pharmaceutically acceptable acid addition salt thereof.

13. A method of treating diabetes according to claim 12 comprising administering to a diabetic host a therapeutically effective amount of a compound wherein $R_o$ is trifluoromethyl in the 4-position and $R_1$ is methyl or ethyl, or a pharmaceutically acceptable acid addition salt thereof.

14. A method of treating diabetes according to claim 1 comprising administering to a diabetic host a therapeutically effective amount of a compound of formula Ic:

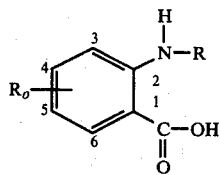

Ic wherein $R_o$ is as defined in claim 1 and R is $C_{2-18}$ alkanoyl or $C_{1-6}$ alkyl, or a pharmaceutically acceptable salt thereof.

15. A method of treating diabetes according to claim 14 comprising administering to a diabetic host a therapeutically effective amount of a compound wherein $R_o$ is chloro, nitro or trifluoromethyl in the 4- or 6-position and R is $C_{2-18}$ alkanoyl, or a pharmaceutically acceptable simple salt thereof.

16. A method of treating diabetes according to claim 15 comprising administering to a diabetic host a therapeutically effective amount of a compound wherein $R_o$ is trifluoromethyl in the 4- or 6-position and R is $C_{2-18}$ alkanoyl, or a pharmaceutically acceptable simple salt thereof.

17. A method of treating diabetes according to claim 14 comprising administering to a diabetic host a therapeutically effective amount of a compound wherein $R_o$ is chloro, nitro or trifluoromethyl in the 4- or 6-position and R is $C_{2-12}$ alkanoyl, or a pharmaceutically acceptable simple salt thereof.

18. A method of treating diabetes according to claim 17 comprising administering to a diabetic host a therapeutically effective amount of a compound wherein $R_o$ is chloro, nitro or trifluoromethyl in the 4-position and R is $C_{2-8}$-alkanoyl, or a pharmaceutically acceptable simple salt thereof.

19. A method of treating diabetes according to claim 18 comprising administering to a diabetic host a therapeutically effective amount of a compound of the formula,

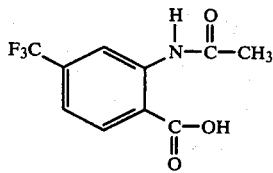

or a pharmaceutically acceptable simple salt thereof.

20. A method of treating diabetes according to claim 18 comprising administering to a diabetic host a therapeutically effective amount of the compound of the formula,

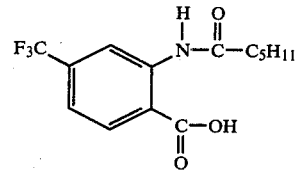

or a pharmaceutically acceptable simple salt thereof.

21. A method of treating diabetes according to claim 14 comprising administering to a diabetic host a therapeutically effective amount of a compound wherein $R_o$ is as defined in claim 14 and R is $C_{2-4}$ alkanoyl or $C_{1-6}$ alkyl, or a pharmaceutically acceptable salt thereof.

22. A method of treating diabetes according to claim 21 comprising administering to a diabetic host a therapeutically effective amount of a compound wherein $R_o$ is chloro, nitro or trifluoromethyl in the 4-position and R is $C_{2-4}$ alkanoyl, or a pharmaceutically acceptable simple salt thereof.

23. A method of treating diabetes according to claim 22 comprising administering to a diabetic host a therapeutically effective amount of a compound wherein $R_o$ is as defined in claim 22 and R is acetyl, or a pharmaceutically acceptable simple salt thereof.

24. A method of treating diabetes according to claim 1 comprising administering to a diabetic host a therapeutically effective amount of a compound of formula Id:

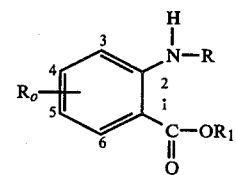

Id wherein $R_o$ is as defined in claim 1, R is $C_{2-18}$ alkanoyl or $C_{1-6}$ alkyl and $R_1$ is $C_{1-12}$ alkyl, or a pharmaceutically acceptable acid addition salt thereof.

25. A method of treating diabetes according to claim 24 comprising administering to a diabetic host a therapeutically effective amount of a compound wherein $R_o$ is chloro, nitro or trifluoromethyl in the 4- or 6-position, R is $C_{2-12}$ alkanoyl and $R_1$ is $C_{1-8}$ alkyl.

26. A method of treating diabetes according to claim 25 comprising administering to a diabetic host a therapeutically effective amount of a compound wherein $R_o$ is chloro, nitro or trifluoromethyl in the 4-position, R is $C_{2-8}$ alkanoyl and $R_1$ is $C_{1-6}$ alkyl.

27. A method of treating diabetes according to claim 24 comprising administering to a diabetic host a therapeutically effective amount of a compound wherein $R_o$ is as defined in claim 24, R is $C_{2-4}$ alkanoyl or $C_{1-6}$ alkyl and $R_1$ is $C_{1-6}$ alkyl, or a pharmaceutically acceptable acid addition salt thereof.

28. A method of treating diabetes according to claim 27 comprising administering to a diabetic host a therapeutically effective amount of a compound wherein $R_o$ is as defined in claim 27, R is $C_{2-4}$ alkanoyl and $R_1$ is $C_{1-6}$ alkyl.

* * * * *

UNITED STATES PATENT AND TRADEMARK OFFICE
CERTIFICATE OF CORRECTION

PATENT NO. : 4,307,113

DATED : December 22, 1981

INVENTOR(S) : Paul L. Anderson

It is certified that error appears in the above-identified patent and that said Letters Patent is hereby corrected as shown below:

Column 7, line 51; before "wherein", insert -- -O-R --.

Column 12; in the table under the column heading "sterile injectable suspension", delete " 80), ".

Column 12, in the table under the column heading "sterile injectable suspension"; after the first occurrence of "q.s.", relocate the word "for" so that it precedes the word "injection" on the following line.

Signed and Sealed this

Eighth Day of March 1983

[SEAL]

Attest:

Attesting Officer

GERALD J. MOSSINGHOFF

Commissioner of Patents and Trademarks